(12) United States Patent
Brophy et al.

(10) Patent No.: US 6,277,630 B1
(45) Date of Patent: Aug. 21, 2001

(54) EXPANDABLE SEQUENCING TRAY

(75) Inventors: John M. Brophy, Taylorsville; West L. Price, Draper; Stephen C. Mackert, Sandy, all of UT (US)

(73) Assignee: Sorenson Bioscience, Inc., Salt Lake City, UT (US)

( * ) Notice: Subject to any disclaimer, the term of this patent is extended or adjusted under 35 U.S.C. 154(b) by 0 days.

(21) Appl. No.: 09/701,672
(22) PCT Filed: May 28, 1999
(86) PCT No.: PCT/US99/12028
 § 371 Date: Nov. 29, 2000
 § 102(e) Date: Nov. 29, 2000
(87) PCT Pub. No.: WO99/61153
 PCT Pub. Date: Dec. 2, 1999

Related U.S. Application Data

(60) Provisional application No. 60/087,328, filed on May 29, 1998.

(51) Int. Cl.[7] .................................................. C12M 1/34
(52) U.S. Cl. ................................. 435/288.4; 435/305.2; 435/809; 422/102
(58) Field of Search .................................... 204/616, 618; 422/102; 435/287.2, 288.4, 305.2, 809

(56) References Cited

U.S. PATENT DOCUMENTS 5,707,506 * 1/1998 Douthart et al. ...................... 204/622
5,916,526 * 6/1999 Robbins ................................ 422/102

* cited by examiner

Primary Examiner—David A. Redding
(74) Attorney, Agent, or Firm—TraskBritt, P.C.

(57) ABSTRACT

A DNA sequencing tray (92) holds an array of sample wells (82) in a rank and file pattern by means of rigid file members (85) connected by flexible mechanisms (87) permitting the pattern to be expanded to change the center-to-center spacing between adjacent wells (82) form 9 mm to 10.8 mm.

14 Claims, 7 Drawing Sheets

EXPANDABLE SEQUENCING TRAY

PRIORITY CLAIM

This application claims the benefit of the filing date of U.S. Provisional patent application Ser. No. 60/087,328, filed May 29, 1998 for "EXPANDABLE ELECTROPHORESIS PLATE."

TECHNICAL FIELD

This invention pertains generally to adjustment of the intersection coordinates of an array characterized by regularly spaced target locations between steps of a procedure applied to the array. It is particularly directed to electrophoresis applications, and provides means for adjusting the spacings between target sites within a conventional sample well array to the spacing pattern of electrophoresis gel wells. The invention has particular application to DNA sequencing procedures.

BACKGROUND ART

Electrophoresis is used for a large number of applications. For example, DNA sequencing can be undertaken to determine the genetic composition, and specifically the nucleotide sequence, of a sample of DNA.

Many existing electrophoresis applications are undertaken using so-called "running tanks." In that procedure, a sample-containing gel is disposed in an electrophoresis chamber in the tank. Electric current is then applied to the gel by means of an electrode in the tank to cause electrophoresis of the sample. In the specific case of DNA sequencing, a thin slab of gel is disposed between two rigid glass plates, and this "gel sandwich" assembly is mounted vertically between upper and lower buffer chambers. A multiple-toothed "comb" structure is inserted into the gel to form "wells" adapted to receive samples. These "gel wells" are of uniform spacing and geometry (formats), as determined by the tooth geometry of the comb. Samples are conventionally deposited into the gel wells by means of nozzle dispensers. The most commonly used dispensers for electrophoresis applications are pipettes or syringes.

Vertical slab gel electrophoresis is the key separation technology used in the human genome effort currently underway. This project proposes to determine the sequencing of the entire human genome of three billion base pair within a five year period. Vertical slab gel electrophoresis, as currently practiced, incorporates an automated fluorescence DNA sequencer.

Sequencing technology has advanced rapidly. Standardization of equipment has been driven by the need for efficiency and reproducibility. A 96 well format has become the standard for manipulating and processing samples in the human genome project. The currently accepted sequencing protocol centers on this same standard 96 well format. This standardization has promoted efficiency in many areas of the human genome project, particularly in procedures involving the use of robotics. The 96 well format has been incorporated in a standardized 96 well sequencing tray, typically comprising a pipette tip rack. This rack has constituted the interface between the sample manipulation and electrophoresis loading steps of the overall procedure.

The loading of DNA samples onto the automated fluorescence DNA sequencer has not yet been automated, and thus remains a very labor intensive portion of the overall process. The loading step has constituted the most tedious part of the sequencing process. Individual samples have typically been deposited into the gel wells with a syringe equipped with a thin wire tip or with a pipette loaded with a flattened plastic tip. Recently, standardization to a 96 well format has facilitated the use of a multiple channel loader, based upon multiple syringes or a multi-channel pipette equipped with disposable tip strips. This multiple channel loading approach has greatly reduced the time and labor required for the loading step.

Samples are conventionally loaded into a sample rack in which individual sample wells are arranged in an array at target locations, each of which may be defined by unique Cartesian coordinates. These target locations are ordinarily disposed in ranks and files on a 96 format pattern; that is, 8 files of 12 ranks each. Advanced techniques involve loading an entire rank of 8 sample wells simultaneously with a multi-channel pipettor. The target locations of the respective sample wells has been standardized to 9 millimeters (mm), as has the spacing of the discharge tips of the multi-channel pipettors used to load those sample wells. The spacings of the comb teeth used to create the gel wells has also been standardized so that either 8 or 12 evenly spaced wells will register with the respective discharge tips of a standardized multi-channel pipettor.

Several standardized combs have evolved, each providing a fixed number of wells, or "lanes." A 36 lane comb produces lanes spaced such that a 9 mm eight-channel pipettor will register a tip with every other lane.; e.g., lanes 1, 3, 5, 7, 9, 11, 13 and 15. A second discharge pass of the pipettor registers with lanes 2, 4, 6, . . . and 16, thereby depositing sample into one half the available gel wells. The remaining half of the lanes (17–32) can then be filled in similar fashion. A 48 lane comb provides lanes spaced such that the nozzles of a 9 mm dispenser head register with every third lane (e.g., lanes 1, 4, 7, . . . and 22). Moving the dispenser head to fill wells at lanes 2 and 3 results in sample deposits into the first 24 wells, again one half the total number available. A 64 lane comb provides lanes spaced such that the 9 mm head registers with every fourth well. Depositing sample into wells 1 through 4 results in sample deposits to 32 wells, again one half the total available. In each case, the second half of the available lanes can be accessed by repeating the procedure applied to the first half of the available lanes.

It has been practical to utilize the sample racks and dispensers utilized for sample preparation in the electrophoresis operation as long as the formats of the sample arrays and gel well patterns have remained based upon the 96 sample well format, with 9 mm spacings. Unfortunately, as the press for greater through put has gained momentum, the spacings between gel wells has been further decreased, and standardization based upon the 96 well format has been abandoned with respect to the electrophoresis operation. Recently, a 96 lane comb has been introduced. While a 9 mm head will register with every fifth lane (1, 6, 11 . . . 36) produced by this comb, deposits to wells 1 through five accounts for a total of 40 lanes. Repeating the procedure accounts for only 80 of the 96 available lanes, leaving 16 lanes which must be accessed by some other means. Reliance upon the conventional 9 mm head is thus inappropriate. Accordingly, there has evolved a new standard multi channel dispenser format for the loading of gel wells produced by the new 96 lane combs. This dispenser has eight nozzles spaced 10.8 mm so that individual dispenser tips access every seventh lane. Deposits into wells 1 through 6 effects deposits into a total of 48 wells, one half the 96 available lanes.

Because the existing standard 96 sample well format does not interface with the 10.8 mm pipette head spacing imposed by the new 96 lane comb used for gel well formation, adoption of this new electrophoresis format imposes a requirement for reformatting the sample array prior to the electrophoresis loading step. This step is relatively labor intensive and time consuming. It also introduces an additional opportunity for error in the overall procedure. It is economically unfeasible to retrofit all of the extant laboratory facilities currently wedded to the 96 well sample format to adopt a 10.8 sample well spacing.

DISCLOSURE OF INVENTION

This invention provides structures that address the incompatibility between conventional 96 sample well array format and the gel well comb pattern format currently being introduced into vertical electrophoresis techniques. While particular emphasis is given to this specific format incompatibility issue, the invention has application to the harmonization of incompatible formats in other applications, both within and unrelated to electrophoresis technologies. The invention provides, in tray format, an array of sample wells organized for loading by a multiple tip pipettor device in conventional fashion. The tray is structured to permit increasing (or reducing) the spacing between adjacent wells, along at least one coordinate axis, to permit sample extraction by a multiple tip pipettor having a different tip spacing than that of the sample-loading pipettor. In an exemplary embodiment, the sample wells are arranged in rows (ranks) and files. The sample wells associated with individual rows are connected in substantially fixed position by means of relatively rigid structural members. These row members are interconnected by mechanisms which allow for adjustment of the spacing between rows. Ideally, the mechanisms connecting respective rows are structured and arranged to provide coordinated movement over the limited range required; that is, the spacings between adjacent rows should remain approximately identical across the array. A preferred form of such mechanisms comprises tethering members (such as flexible hinges or strands) The invention further contemplates a novel multi tip pipettor in which the spacings between adjacent tips is 10.8 mm. It also contemplates a novel rack with individual well sockets spaced and arrange to accept and hold an expanded tray of the invention..

The invention may thus be typified by an adjustable DNA sequencing tray comprising a plurality of relatively rigid structural members arranged in spaced, parallel relation, each such structural member carrying a plurality of sample wells in spaced file arrangement such that the sample wells carried by the tray are arranged in a rank and file pattern. Preferably, linkage mechanism connecting adjacent such rigid structural members are structured and arranged selectively to hold the sample wells in that pattern in adjustable fashion between a first condition in which the center-to-center spacing between sample wells in adjacent such rigid structural members is a relatively small distance, and a second condition in which that center-to-center spacing is a relatively larger distance. Ideally, the linkage mechanism functions to establish the relevant center-to-center spacing at approximately 9 mm when the pattern is set at its first condition and at approximately 10.8 mm when that pattern is set at its second condition An ideal linkage structure comprises tether strands with memory biasing the pattern to its first condition.

BRIEF DESCRIPTION OF THE DRAWINGS

In the drawings, which illustrate what applicant currently regards as the best mode for carrying out the invention.

BEST MODE(S) FOR CARRYING OUT THE INVENTION

Figure 1:
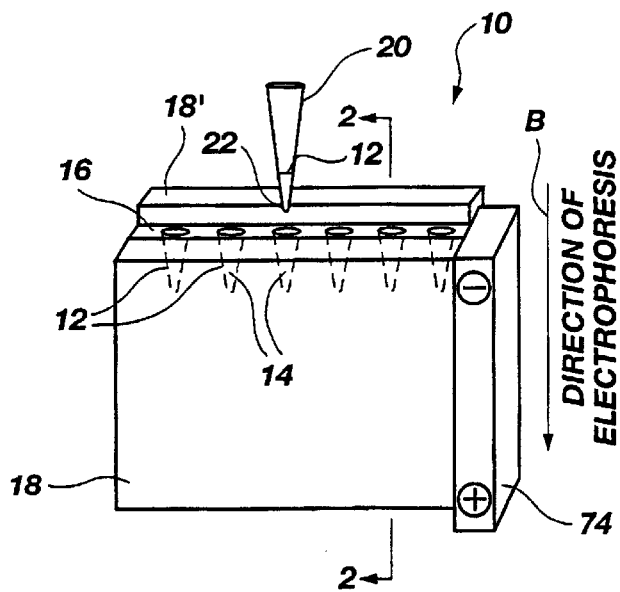
FIG. 1 is a pictorial schematic representation of known apparatus for conducting vertical electrophoresis.
Figure 2:
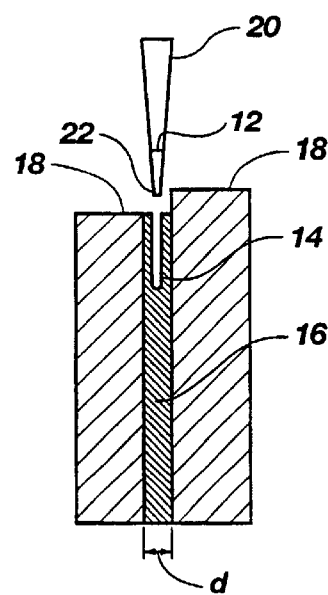
FIG. 2 is a cross sectional view of the apparatus of FIG. 1, taken along the section line 2—2, looking in the direction of the arrows.

FIGS. 1 and 2 illustrate an electrophoresis device, generally 10, receiving biological sample material 12 in individual gel wells 14 formed within a thin film 16 of sequencing gel held sandwiched between spaced structural plates 18. A potential is applied across the gel by means of a fixture 19. Charge-carrying molecules forming the sample 12 migrate downwardly in the direction of arrow B, and are separated under the influence of the applied voltage in accordance with their respective molecular weights. The samples 12 are dispensed into individual wells 14 by individual micro pipette tips 20, which are conventionally carried by the head of a pipettor (not shown). The plates 18 are separated by a distance d (FIG. 2), which is typically quite small; e.g., 0.20 mm.

Figure 3:
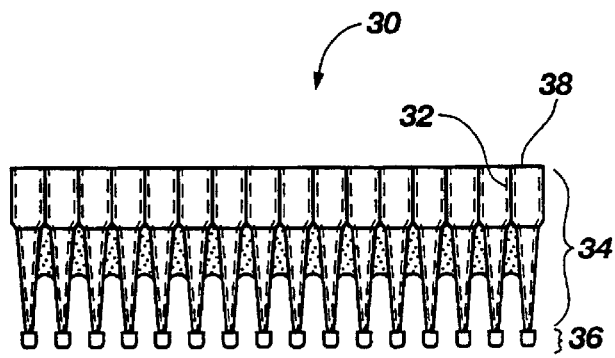
FIG. 3 is a view in elevation of a pipette tip strip useful with multi-channel dispensers.

FIG. 3 illustrates one embodiment of a pipette tip device, generally 30. A plurality of interconnected tips 32 are disposed in substantially parallel orientation and in side-by-side alignment. The tips 32 are hollow, and each comprises a tip body 34 and a flattened tip extremity 36. These extremities 36 occupy a common plane, and are spaced to register simultaneously with individual gel wells 14. An interior bore extends through each tip 32 from an open upper end 38 through the distal extremity 36. Samples may be loaded by a technician into each of the tips 32. The individual tips 32 of the device 30 may then be registered into individual wells 14, and the samples 12 dispensed simultaneously, typically relying upon a syringe, pipettor or similar dispensing device to displace the samples 12 from the tips 32.

Figure 4:
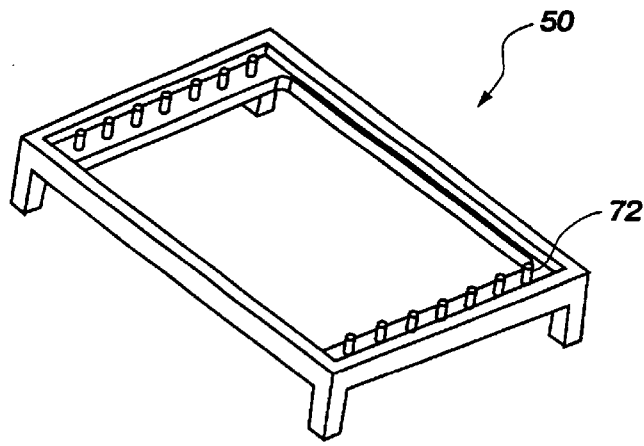
FIG. 4 is a pictorial view of a holding rack useful for holding tip strips such as those of FIG. 3 in a 96 well format.
Figure 5:
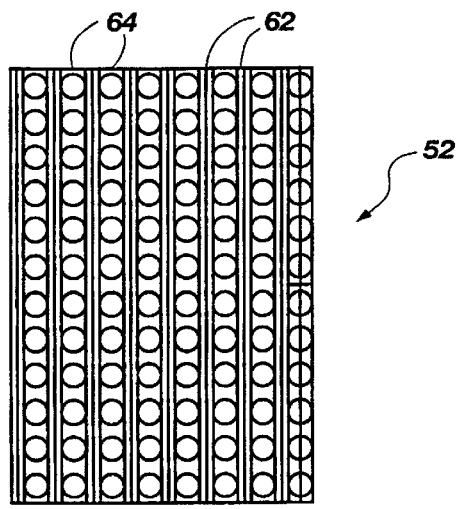
FIG. 5 is top plan view of a sample well template of the invention collapsed to a conventional 96 well format and loaded with sample wells.
Figure 7:
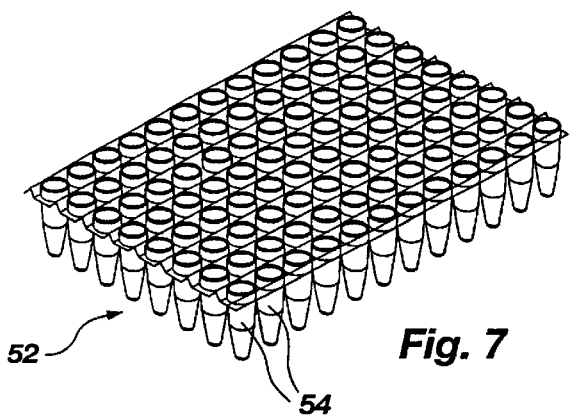
FIG. 7 is a pictorial view of the loaded sample well template of FIG. 5.
Figure 6:
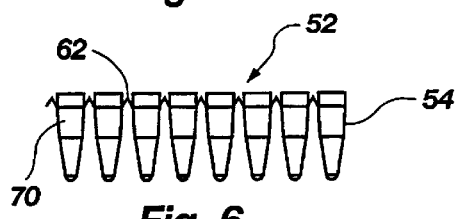
FIG. 6 is a view in elevation of a short side of the loaded sample well template of FIG. 5.
Figure 8:
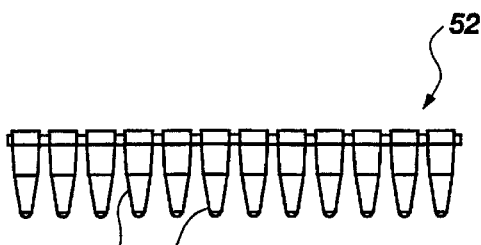
FIG. 8 is a view in elevation of a long side of the loaded sample well template of FIG. 5.
Figure 9:
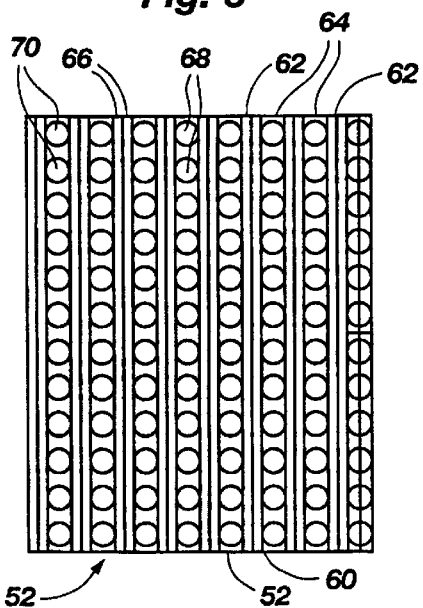
FIG. 9 is a plan view similar to FIG. 5, showing the sample well template in expanded condition.
Figure 10:
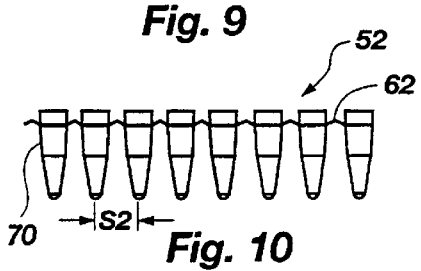
FIG. 10 is a view in elevation similar to FIG. 6 of the sample well template expanded as shown by FIG. 9.
Figure 11:
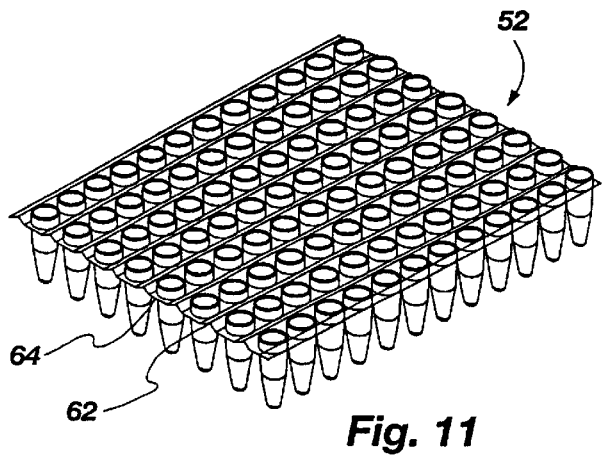
FIG. 11 is a pictorial view similar to FIG. 7 of the sample well template expanded as shown by FIGS. 9 and 10.
Figure 12:
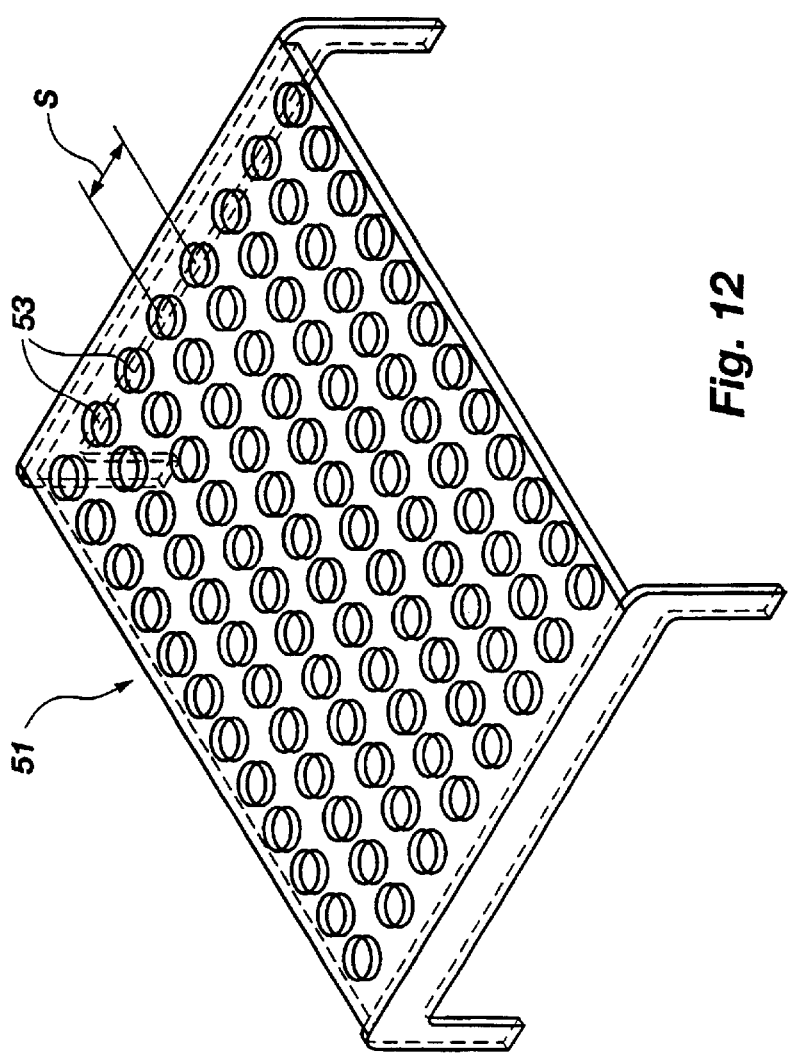
FIG. 12 is a perspective view of a holding rack for use with the template of FIGS. 5–11.

A rack, generally 50, such as that of FIG. 4, is conventionally to support a plurality of strips of the type illustrated by FIG. 3. A similar structure may be used to support certain embodiments of this invention, as will be explained in connection with FIGS. 13 and 14. A support rack, generally 51, of the type illustrated by FIG. 12, may be used in connection with the sequencing tray, generally 52 of FIGS. 5–11. The sequencing tray 52 constitutes both a sample plate and an electrophoresis plate. FIGS. 5–8 show the sequencing tray 52 in a first, collapsed condition, in which the array of individual sample wells 54 are spaced a distance SI, for example 9 mm. This spacing is determined by the distance S between individual sockets 53 in the rack 51. FIGS. 9–11 illustrate the same sequencing tray 52 as it would be expanded by mounting it in a rack 51 in which the distance S was increased. In expanded condition, the spacing S2 between sample wells 54 is enlarged; e.g., to 10.8 mm. This expansion is effected through linkage elements 62 between file structures 64. As illustrated, the linkage structures 62 comprise "living hinge" elements defined by three parallel fold lines 66, each of which may, for example, constitute a thinned crease in a plastic (e.g., standard polypropylene) sheet constituting the sequencing tray 52. Each file structure 64 presents a line of target sites 68, shown occupied by individual sample wells 70. These sites 68 are illustrated as organized into ranks disposed normal to the files, although other arrangements are within contemplation.

Other embodiments connect the file structures with other mechanical means, such as slides, which permit adjustment of the sample well spacings from a collapsed distance S1 to an expanded distance S2. Still other embodiments may provide for adjustment of rank structures in addition to file structures, thereby to adjust the spacings of sample wells along both file and rank coordinate locations (both the x and y Cartesian axes).

Figure 14:
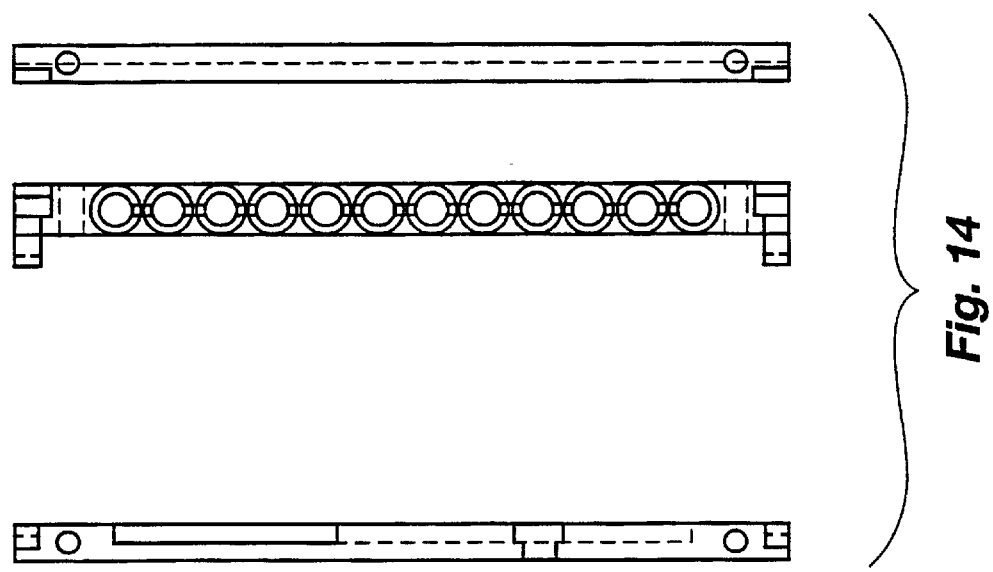
FIG. 14 is a fragmentary drawing illustrating certain component parts of the embodiment of FIG. 12.
Figure 13:
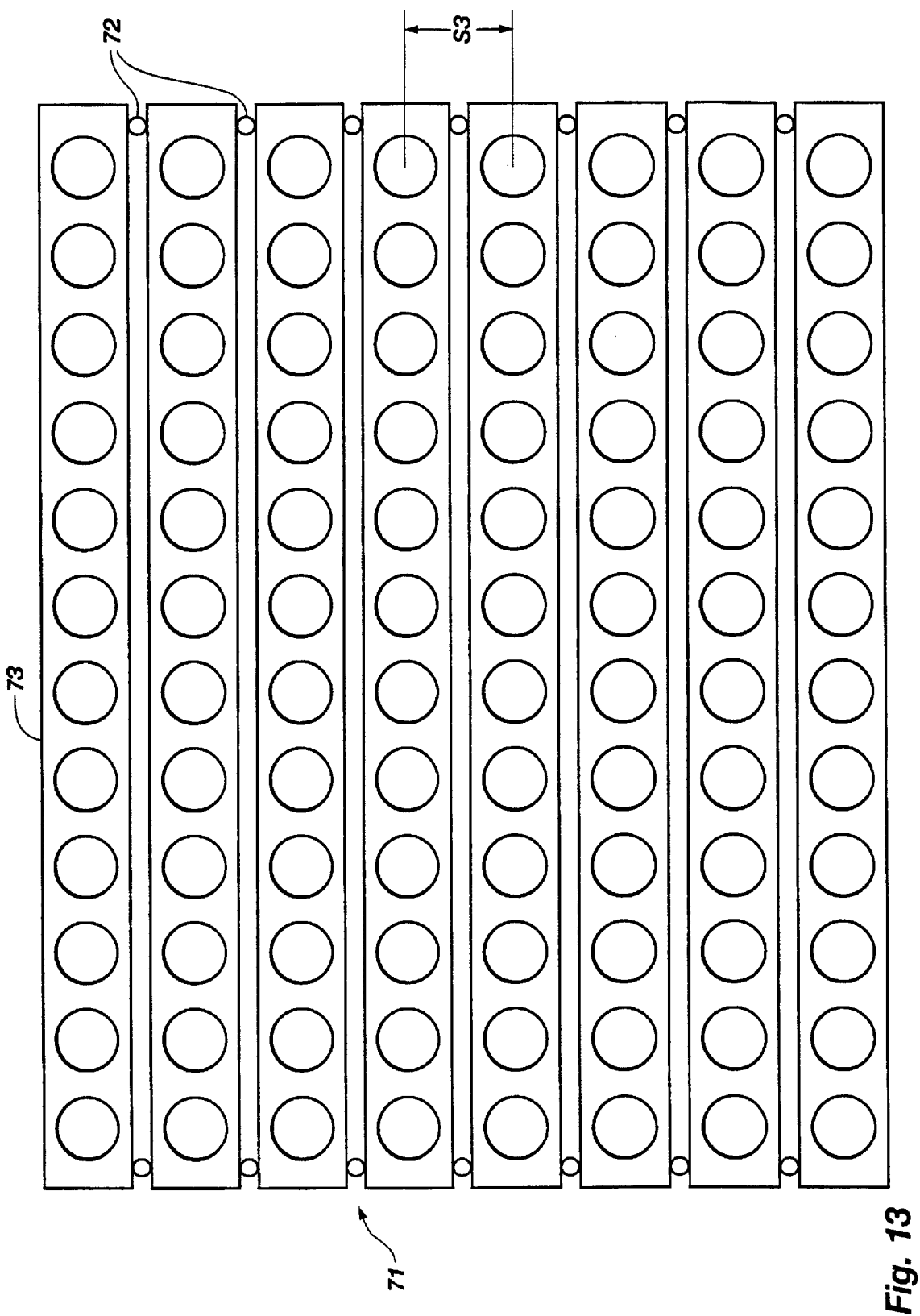
FIG. 13 is a top plan view of an alternative embodiment of the invention.

FIG. 13 partially illustrates an assembly, generally 71, adapted for support by a rack of the type illustrated by FIG. 4. The rack includes upstanding pegs 72. The assembly 71 comprises a plurality of rigid perforated rails 73, each of which constitutes a file member similar to the file members 64 of the earlier-described embodiment. The rails 73 are connected by slides (not shown) or similar mechanical linkages which permit them to be separated and installed in the rack 50 with pegs 72 separating individual rails 73 as shown. The distance S3 is adjustable, for example between 9 mm (with the rails 73 tightly adjacent each other) and 10.8 mm (as illustrated) FIG. 14 illustrates typical components suitable for fashioning an assembly 71.

Figure 15:
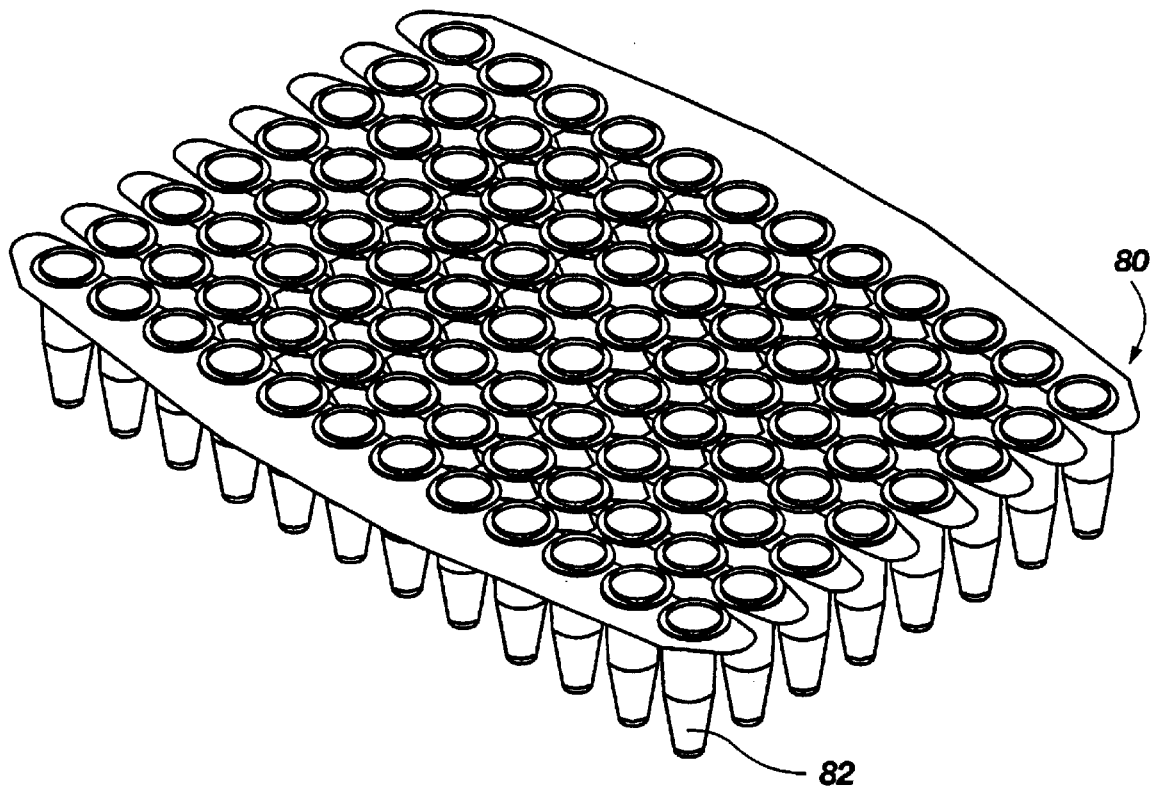
FIG. 15 is a pictorial view of an expandable sequencing tray of the invention.
Figure 16:
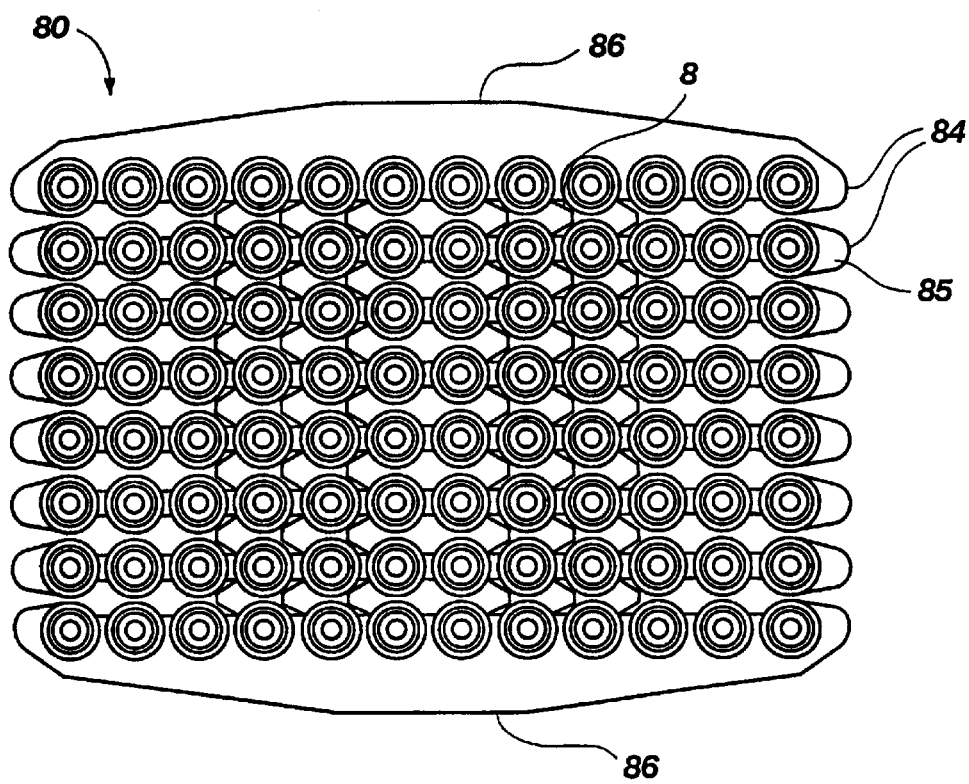
FIG. 16 is a top plan view of the tray of FIG. 15.

FIGS. 15 and 16 illustrate a presently preferred embodiment, generally 80, in which individual sample wells 82 are arranged in rows 84. Each row 84 comprises the wells 82 carried by an individual file structure constructed as a relatively rigid structural member 85. A typical construction material for these members 85 is medical grade plastic. The outer members 85 are formed with integral tab extensions 86 shaped to accommodate grasping by a technician's fingers. The tray 80 is illustrated in a first, unexpanded (or relaxed) condition with the center-to-center spacings between the wells 82 of adjacent members 85 fixed at approximately 9 mm. Adjacent members 85 are connected by tether strands 87, each of which functions as a weak spring biased to the relaxed condition illustrated.

Figure 17:
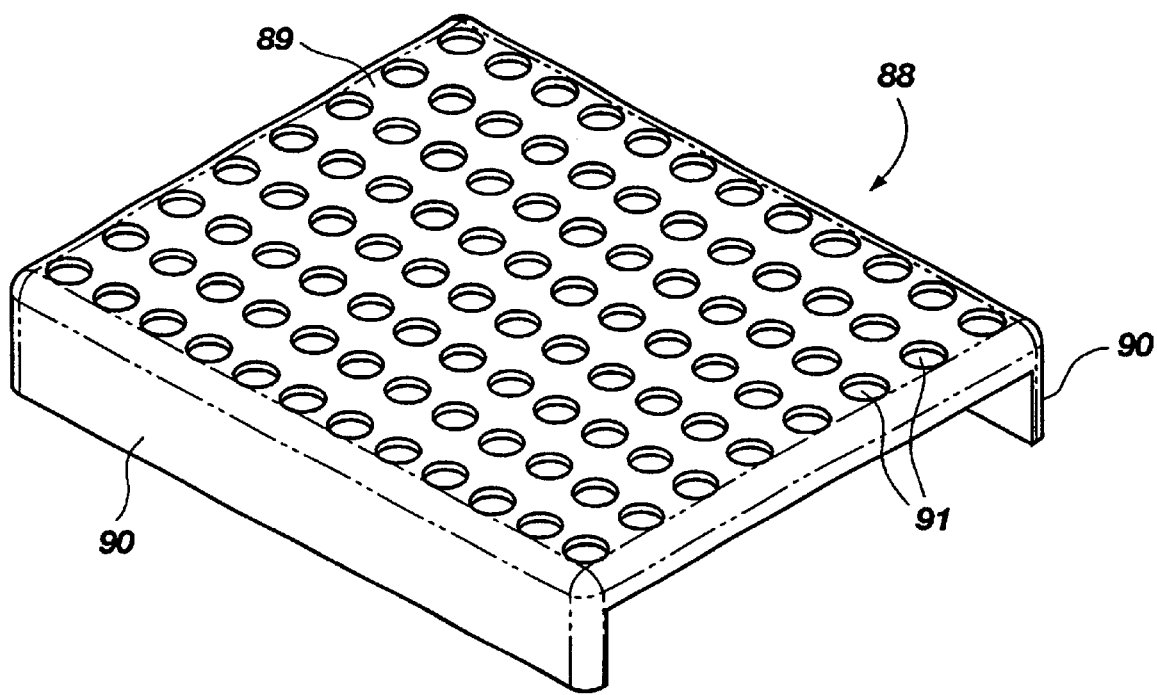
FIG. 17 is a pictorial view of a rack structured to accept the tray of FIG. 15 in its expanded condition.

The rack, generally 88, of FIG. 17 includes a perforated plate 89 supported by side rails 90. The center-to-center spacings of adjacent sockets 91 carried by the plate 89 is approximately 10.8 mm. In use, the wells 82 may be loaded wit sample material by means of a conventional multi-tip device, such as a pipettor with nozzles spaced at 9 mm. The loaded tray 80 may then be reconfigured to a second, expanded, condition by applying modest spreading force to the tabs 86, against the memory bias of the tether strands 87, thereby increasing the distance between adjacent wells 82 to approximately 10.8 mm. The wells 82 of the tray 80 may then be positioned within the sockets 91 of the tray 88.

Figure 18:
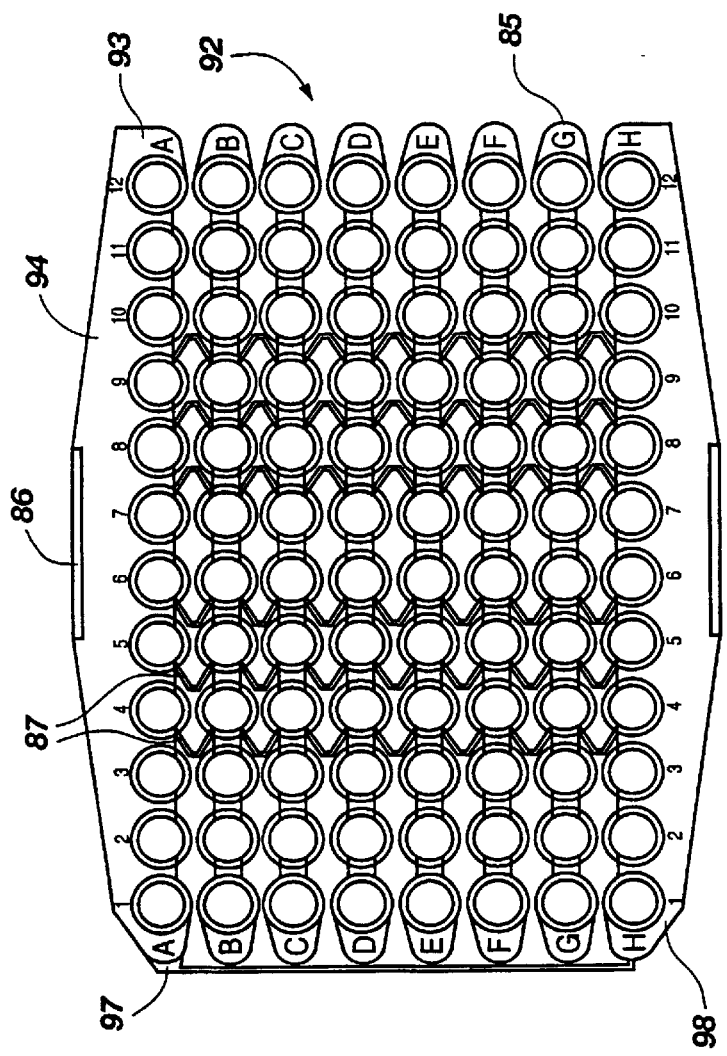
FIG. 18 is a top plan view similar to FIG. 16, but of an alternative embodiment.
Figure 19:
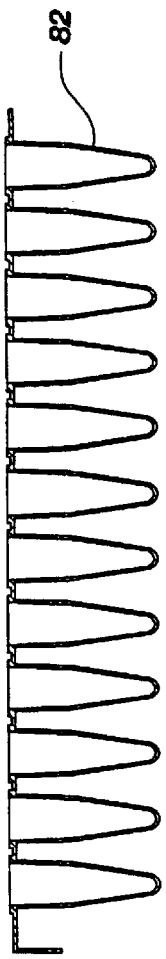
FIG. 19 is a view in side elevation of the embodiment of FIG. 18.
Figure 20:
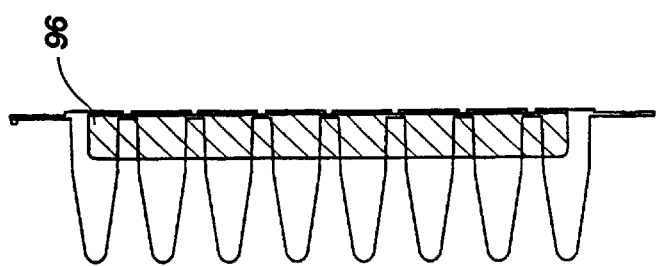
FIG. 20 is a n end view, in elevation of the embodiment of FIG. 18.

FIGS. 18, 19 and 20 illustrate a sequencing tray, generally 92, similar to that of FIGS. 15 and 16, with various indicia and structures useful for maintaining correct orientation and identification of the sample wells 82. Each row is assigned a number designation, 93, ranging from "A" to "H." Each rank is assigned a numeric designation, 94, ranging from "1" to "12." In this fashion, each individual well 82 ma be distinguished by a unique Cartesian address. A structural tab 96 attached at one corner location 97 at one end of the tray 92 is provided for visual or machine-readable (e.g., bar codes) indicia. The corners 97, 98 at one end of the tray 92 are shaped for easy recognition and indexing. These index corners 97, 98 avoid symmetry, thereby avoiding confusion concerning the proper orientation of the tray 92 in use. Tether strands 87 are provided in the central portion of the tray 92, in the vicinity of the tabs 86. In practice, this arrangement provides for adequate connection to maintain approximately parallel orientation of adjacent members 85 in both relaxed and expanded condition of the tray 92.

INDUSTRIAL APPLICATION

The invention finds current application in processes involving massive electrophoresis procedures. It is especially useful for DNA sequencing procedures.

What is claimed is:

1. An adjustable sample well tray comprising:
    a plurality of file members arranged in spaced, parallel relation, each carrying a plurality of target locations spaced along a line;
    adjacent said file members being connected by linkage structure adapted selectively to assume:
        a first, relaxed, condition in which the spacing between adjacent target sites in adjacent said file members are separated by a first, relatively small distance and
        a second, expanded, condition in which said spacings between adjacent target sites of adjacent said file members are separated by a second, relatively large distance.

2. An adjustable sample well tray according to claim 1, wherein said linkage structure comprises a living hinge arrangement.

3. An adjustable sample well tray according to claim 1, wherein said linkage structure comprises tether strands with memory bias to said relaxed condition.

4. An adjustable sample well tray according to claim 1, wherein said target locations comprise the centers of respective sample wells, and said linkage structures function such that the center-to-center distance between said sample wells in adjacent said file members is approximately 9 mm with said tray in said relaxed condition.

5. An adjustable sample well tray according to claim 4, wherein said linkage structure comprises a living hinge arrangement.

6. An adjustable sample well tray according to claim 4, wherein said linkage structure comprises tether strands with memory bias to said relaxed condition.

7. An adjustable sample well tray according to claim 4, wherein said linkage structures function such that the center-to-center distance between said sample wells in adjacent said file members is approximately 10.8 mm with said tray in said expanded condition.

8. An adjustable sample well tray according to claim 7, wherein said linkage structure comprises a living hinge arrangement.

9. An adjustable sample well tray according to claim 7, wherein said linkage structure comprises tether strands with memory bias to said relaxed condition.

10. An adjustable DNA sequencing tray comprising:
   a plurality of relatively rigid structural members arranged in spaced, parallel relation, each said structural member carrying a plurality of sample wells in spaced file arrangement such that the sample wells carried by said tray are arranged in a rank and file pattern;
   linkage mechanism connecting adjacent said rigid structural members and being structured and arranged selectively to hold said sample wells in said pattern in adjustable fashion between:
      a first condition in which the center-to-center spacing between sample wells in adjacent said rigid structural members is a relatively small distance, and
      a second condition in which said center-to-center spacing is a relatively larger distance.

11. A sequencing tray according to claim 10, wherein said linkage mechanism functions to establish said center-to-center spacing at approximately 9 mm when said pattern is set at said first condition and at approximately 10.8 mm when said pattern is set at said second condition.

12. A sequencing tray according to claim 11, wherein said linkage structure comprises a living hinge arrangement.

13. A sequencing tray according to claim 11, wherein said linkage structure comprises tether strands with memory biasing said pattern to said first condition.

14. A sequencing tray according to claim 11 wherein said pattern includes 96 said sample wells, arranged in eight files of 12 ranks.

* * * * *